US00PP29395P2

(12) United States Plant Patent
Hansen

(10) Patent No.: US PP29,395 P2
(45) Date of Patent: Jun. 12, 2018

(54) ***HEUCHERA* PLANT NAMED 'BLACK PEARL'**

(50) Latin Name: ***Heuchera* hybrid**
Varietal Denomination: Black Pearl

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days. days.

(21) Appl. No.: 15/530,032

(22) Filed: Nov. 21, 2016

(51) Int. Cl.
*A01H 5/12* (2018.01)
*A01H 5/02* (2018.01)

(52) U.S. Cl.
USPC ..... Plt./440
CPC ..... *A01H 5/02* (2013.01); *A01H 5/12* (2013.01)

(58) Field of Classification Search
USPC ..... Plt./440
CPC . A01H 5/02; A01H 5/025; A01H 5/12; A01H 5/00
See application file for complete search history.

(56) References Cited

PUBLICATIONS

Michell's 2015-16 Availability List Walters Gardens, Inc. retrieved on Nov. 28, 2017, retrieved from the Internet at http://www.michells.com/availabilities/Waltersavailability.pdf, pp. 1, 15 and 28 (Year: 2016).*

* cited by examiner

*Primary Examiner* — June Hwu

(57) ABSTRACT

The new and distinct hybrid of *Heuchera* plant named 'Black Pearl' with foliage of glossy, dark mahogany-purple, scalloped ruffled margins, rosy purple underside and no silver or dark green marbling surrounding the veins. 'Black Pearl' is topped with heavily-branched panicles of overall pink flowering effective over a long period. The new plant is vigorous, compact in habit and tolerates heat and humidity well.

1 Drawing Sheet

Botanical denomination: *Heuchera* hybrid.
Variety denomination: 'Black Pearl'.

BACKGROUND OF THE INVENTION

The present invention relates to a new and distinct cultivar of Coral Bells in the Saxifragaceae family and given the cultivar name of 'Black Pearl'. *Heuchera* 'Black Pearl' was hybridized by the inventor on Apr. 11, 2013 at a wholesale perennial nursery in Zeeland, Mich., USA and initially assigned the breeder code 13-726-1. The seed or female parent was a proprietary unreleased hybrid known only by the breeder code 12-317-04 (not patented) and the pollen or male parent was a proprietary unreleased hybrid known only by the breeder code 11-29-01. The new invention has a mixture of *Heuchera americana, H. brizoides, H. micrantha* and *H. villosa* in the pedigree.

*Heuchera* 'Black Pearl' was first selected in the fall of 2013 and passed final evaluation in the fall of 2014 from among thousands of other seedlings from the same cross and hundreds of other crosses. *Heuchera* 'Black Pearl' has been asexually propagated by division at the same nursery in Zeeland, Mich. in 2014 and by careful shoot tip tissue culture propagation, and the resultant plants have remained stable and continued to exhibit the same characteristics as the original plant for multiple generations.

No plants of *Heuchera* 'Black Pearl' have been sold, in this country or anywhere in the world, prior to the filing of this application, nor has any disclosure of the new plant been made prior to the filing of this application with the exception of that which was disclosed within one year of the filing of this application, and was either derived directly or indirectly from the inventor.

BRIEF SUMMARY OF THE INVENTION

In comparison to both of the parents, *Heuchera* 'Black Pearl' has darker grayed-purple foliage with more intense ruffling of leaf margins and larger leaf blades than the female parent with slightly lighter dark grayed-purple foliage and slightly less intense ruffling. Neither the male parent nor photographs of the male parent have been maintained. Further comparison is not possible. Other similar coral bells include: 'Black Taffeta' U.S. Plant Pat. No. 26,162 which has foliage with similar ruffling but not as dark, and the flower of the new plant has predominantly white petals with pink calyxes; 'Obsidian' U.S. Plant Pat. No. 14,836 has foliage not quite as dark black-purple as the new plant, lacks the ruffling of the leaf margins and has creamy-white flowers compared to the more coral-coloring effect from the predominantly white flower petals and pink calyxes of 'Black Peal'; 'Ruffles 'n Truffles' U.S. Provisional Application No. 62/392,988 has similar ruffling of the foliage, but the coloration is not as dark; 'Bella Notte' U.S. Plant Pat. No. 24,291 has flatter leaves with no ruffling of the foliage, the top surface is not as shiny and the coloration is not as dark as the new plant; 'Midnight Ruffles' U.S. Plant Pat. No. 25,605 has shiny ruffled foliage, but the coloration is more red and the flower color is brownish; 'Dark Chocolate' U.S. Plant Pat. No. 23,454 has lighter foliage with silver marbling.

*Heuchera* 'Black Pearl' differs from its parents as well as all other coral bells known to the applicant in the following combined traits:

1. The foliage color is a glossy, dark, mahogany-purple with rich raspberry underneath.
2. Mid-summer the new plant produces an airy scape of predominantly white flower petals with pink calyxes.
3. The new leaf margins axe very ruffled to contrast with the flat leaf center.
4. The new plant produces large clumps and many large individual leaves.
5. The new plant is vigorous, compact in leaf habit and tolerates heat, sun and humidity.

BRIEF DESCRIPTION OF THE DRAWING

The photograph of the new plant demonstrates the overall appearance of the plant including the unique traits. The colors are as accurate as reasonably possible with color reproductions. Some slight variation of color may occur as a result of lighting quality, intensity, wavelength, and direction or reflection.

FIG. 1 shows a one-year-old plant in a container just before flowering.

DETAILED BOTANICAL DESCRIPTION

The following description is based on a two-year-old plant growing in greenhouse at a nursery in Zeeland, Mich., USA. The new plant has not been grown under all possible environments and may phenotypically appear different under different conditions such as light, temperatures, fertilizer, and water, without any difference in genotype. The color descriptions used are from the 2001 edition of The Royal Horticultural Society Colour Chart except where common dictionary terms are used.

Parentage: Female or seed parent was the proprietary unreleased hybrid known only by the breeder code 12-317-04 (not patented) and the pollen or male parent was a proprietary unreleased hybrid known only by the breeder code 11-29-01; the female parent's lineage is ('Dark Mystery' (not patented)×'Fire Chief' U.S. Plant Pat. No. 21,880 and the male parentage can be further described as ['Mocha' (U.S. Plant Pat. No. 18,386)×'Pwheu0109' known by the tradename of 'Dolce Black Currant' (U.S. Plant Pat. No. 19,574)]×['Dark Chocolate'];

Plant habit: Hardy herbaceous perennial with basal rosette of foliage; mounded foliage about 30 cm tall and 48 cm in diameter with scapes to about 75 cm long; stems to about 12.0 cm long and 2.0 cm diameter at base with about 20 to 28 leaves per stem and seven main stems per plant;

Roots: Fibrous, finely branched;

Growth rate: Rapid, rooting from cutting in two weeks and finishing in three-liter container in about 3 months;

Foliage: Cordate, minutely puberulent adaxial and abaxial; palmately shallowly lobed with five main lobes dissected less than one-third the way to petiole; apex rounded, base cordate to auriculate with basal lobes overlapping about 0.5 cm; margins crenate to mucronate, hirsutulous, crisped to sinuate; lustrous adaxial and abaxial; held nearly horizontal;

Leaf blade size: To about 12.5 cm wide and 13.5 cm long, average about 11.5 cm wide and 12.0 cm long;

Leaf color: Spring and young emerging leaves adaxial nearest RHS 147A with undertone of RHS N186D and with slight silver marbling only as a juvenile plant for approximately a month following transplant from tissue culture and then becoming solid colored with no silver or dark green marbling surrounding the veins, spring young emerging leaves abaxial between RHS N186D and RHS 187C; mature mid-season leaves adaxial nearest RHS N186A with no marbling of silver or darker green surrounding the veins, abaxial mature mid-season leaves nearest RHS N186C; cauline leaves adaxial darker than RHS 147A and abaxial between RHS N187A and RHS N187B; mid-winter adaxial color nearest a blend between RHS N186A and RHS 187A; mid-winter abaxial color nearest RHS N79A;

Leaf quantity: Dense, about 160 per plant;

Veins: Palmate, hirsutulous abaxial and adaxial; costate abaxial, slightly impressed adaxial;

Vein color: On emerging or early spring foliage adaxial blend between RHS 174D and RHS 182D with emerging or early spring abaxial between RHS 186C and RHS 186B; mid-season and flowering time adaxial between RHS 187C and RHS 187B, mid-season and flowering time abaxial between RHS N186D and RHS 71A;

Petiole: Terete to slightly applanate just before base with base amplexicaul; with pubescent hairs to about 2.0 mm long; average about 15.0 cm long and about 4.0 mm diameter in center and 18.0 mm at base including stipule;

Petiole color: Emerging leaf blend between RHS 186C and RHS N186D; mature leaf near base of petiole nearest RHS 194D with overtones of nearest RHS 186C, distally nearest RHS 187B with dark adaxial stripe of nearest RHS 187A;

Stipule: At base of petiole, about 1.3 cm long and about 1.8 cm wide at base;

Stipule color: Adaxial nearest RHS N79C, abaxial between RHS 185D and RHS 186C;

Peduncle: Panicle; terete; stiff; pubescent; upright; to about 75.0 cm long and 5.0 mm diameter at base, average about 62 cm tall and 4.0 mm diameter; about fourteen per plant with up to 590 flowers per panicle, average about 480; heavily-branched panicle with up to 23 branches up to 22 cm long and 1.5 mm diameter decreasing distally, average 20 branches per panicle; branches semi-drooping distally; flower density is dense;

Flowering longevity: Panicle effective for about four to five weeks;

Peduncle color: Young developing nearest RHS 187A, mature nearest RHS N186C;

Pedicel: Terete, finely puberulent, about 2.0 mm long and 0.5 mm diameter;

Pedicel color: Between RHS N186B and RHS 187A;

Buds one day prior to opening: Globose; rounded apex and attenuate base; puberulent to glandular; about 4.4 mm long and 4.0 mm diameter;

Bud color one day prior to opening: Basal portion nearest RHS 186A, becoming nearest RHS 186D in distal one half with apex nearest RHS 137C;

Flower: Perfect, campanulate, actinomorphic, about 8.0 mm long and 4.0 mm in diameter at face; individual flowers lasting about 4 days on plant or as cut flower;

Flower attitude: Outward and drooping;

Calyx: Five, apex rounded, base fused in proximal 3.5 mm to form hypanthium; pubescent abaxial, glabrous adaxial; about 5.5 ram long and 4.0 mm wide;

Calyx color: Abaxial base between RHS 177D and RHS 182D, distally lightening to lighter than RHS 182D; adaxial nearest RHS 182D; green apical tip abaxial and adaxial nearest RHS 138C;

Petals: Five, oblanceolate to spatulate, rounded apex and attenuate base, entire, glabrous abaxial, puberulent adaxial, about 2.5 mm long and 1.0 mm wide in middle;

Petal color: Abaxial lighter than RHS N155D, adaxial nearest RHS 75D;

Androecium: Five adnate to adaxial petal about 1.0 mm from base;

*Filaments*.—Five, thin, glabrous; about 2.5 mm long and less than 0.3 mm diameter; color white, lighter than RHS 155D.

*Anthers*.—Ellipsoidal, distinct, basifixed, longitudinal; color nearest RHS 25B;

*Pollen*.—Abundant; color nearest RHS N25A.

Gynoecium: One, two-beaked; half-inferior; bifid style with pistil split at ovary; 6.0 mm long;

*Style*.—Bifid; split apart at apex of ovary; about 4.5 mm long and about 1.0 mm diameter; color lighter than RHS 182D.

*Stigma*.—Acute apex, about 0.1 mm diameter; color lighter than RHS 182D.

*Ovary*.—Half-inferior, about 2.5 mm long and 2.0 mm diameter; ellipsoidal to globose, base rounded; color nearest RHS 150D.

Fruit: Two-beaked ellipsoidal capsule; about 3.1 mm long and 2.5 mm in diameter at widest portion; color lighter than RHS 164D when mature;

Seed: Ellipsoid; less than about 1.0 mm long and less than about 0.5 mm wide; color between RHS 202A and RHS 200A;

Disease and pest tolerance: The new plant grows best with ample moisture and drainage in either sun or shade. It is more tolerant of hot and humid environments than typical coral bells. Cold hardy from USDA zones 4 to 9. Other resistance and tolerance outside of that normal for *Heuchera* is not known.

It is claimed:

1. The new and distinct coral bells plant named *Heuchera* 'Black Pearl' as herein described and illustrated.

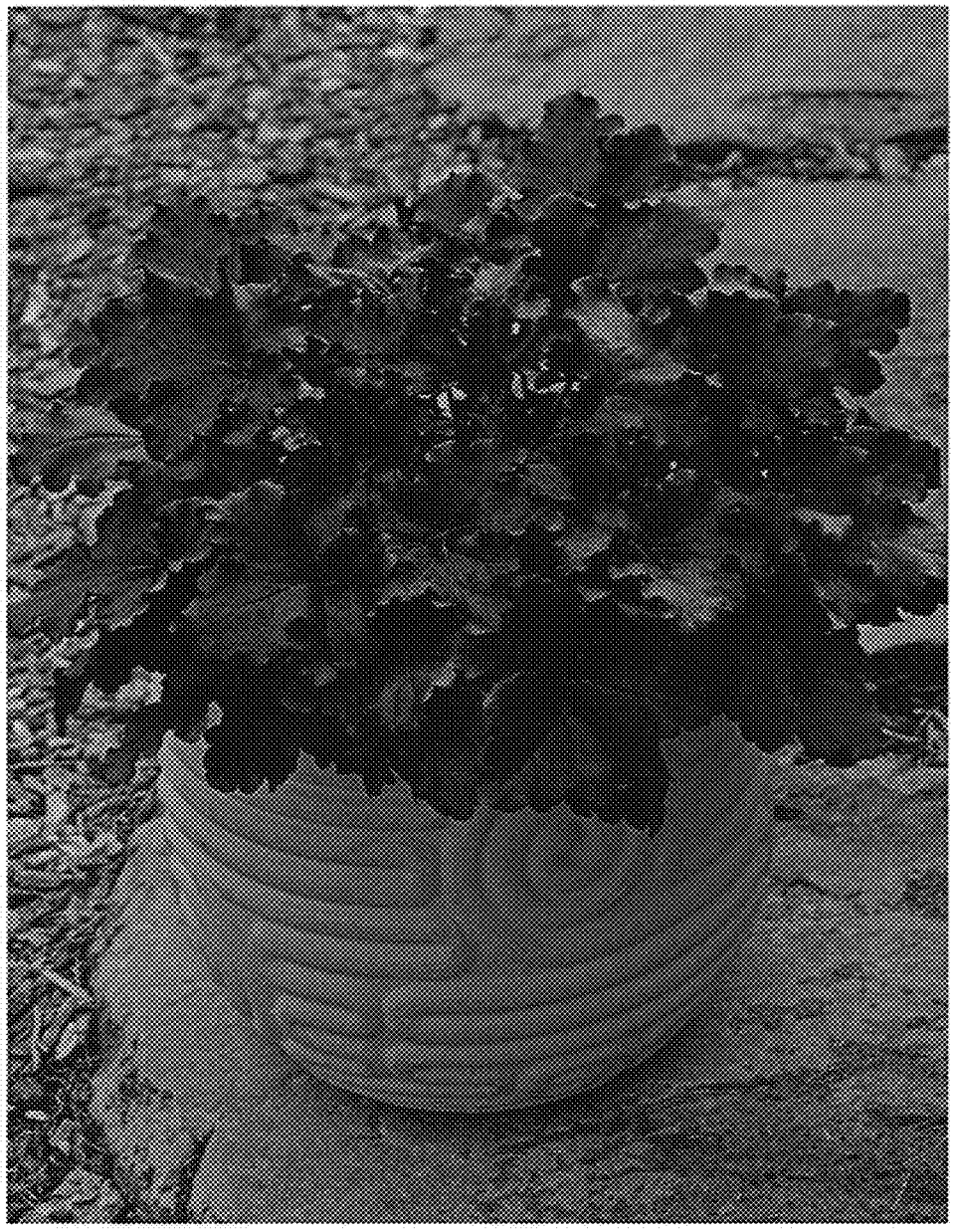

* * * * *